US011649204B2

(12) United States Patent
Lodha et al.

(10) Patent No.: US 11,649,204 B2
(45) Date of Patent: May 16, 2023

(54) PROCESS FOR THE PREPARATION OF TRIFLOXYSTROBIN

(71) Applicant: HIKAL LIMITED, Pune (IN)

(72) Inventors: Kamlesh Kantilal Lodha, Pune (IN); Sandip Popatrao Udawant, Pune (IN); Deepak Babasaheb Phasage, Pune (IN); Lakonda Nagaprasada Rao, Pune (IN); Santosh Kumar Ghosh, Pune (IN); Sudhir Nambiar, Pune (IN)

(73) Assignee: Hikal Limited, Pune (IN)

( * ) Notice: Subject to any disclaimer, the term of this patent is extended or adjusted under 35 U.S.C. 154(b) by 213 days.

(21) Appl. No.: 16/645,605

(22) PCT Filed: Aug. 30, 2018

(86) PCT No.: PCT/IN2018/050560

§ 371 (c)(1),
(2) Date: Mar. 9, 2020

(87) PCT Pub. No.: WO2019/049167

PCT Pub. Date: Mar. 14, 2019

(65) Prior Publication Data

US 2020/0283373 A1 Sep. 10, 2020

(30) Foreign Application Priority Data

Sep. 11, 2017 (IN) ............................ 201721032019

(51) Int. Cl.

| | |
|---|---|
| *C07C 249/08* | (2006.01) |
| *C07C 249/12* | (2006.01) |
| *B01J 31/02* | (2006.01) |
| *C07C 245/20* | (2006.01) |

(52) U.S. Cl.
CPC ......... *C07C 249/08* (2013.01); *B01J 31/0237* (2013.01); *C07C 245/20* (2013.01); *C07C 249/12* (2013.01); *B01J 2231/005* (2013.01); *B01J 2531/002* (2013.01)

(58) Field of Classification Search
None
See application file for complete search history.

(56) References Cited

U.S. PATENT DOCUMENTS

| | | | |
|---|---|---|---|
| 5,238,956 | A | 8/1993 | Clough et al. |
| 6,444,850 | B1 | 9/2002 | Pak et al. |
| 6,670,496 | B1 | 12/2003 | Waditschatka |

FOREIGN PATENT DOCUMENTS

| | | | |
|---|---|---|---|
| CN | 103787916 | * | 5/2014 |
| WO | 2013144924 | A1 | 10/2013 |
| WO | 2017085747 | A2 | 5/2017 |

OTHER PUBLICATIONS

Google Translate translation of Chai ("Study on the Synthesis of Trifloxystrobin"Agrochem. 52(4), p. 258-259, 262, Apr. 2013, of record in the IDS filed on Aug. 11, 2020) (Year: 2013).*
Beech ("Preparation of Aromatic Aldehydes and Ketones from Diazonium Salts" J. Chem. Soc. 1954, p. 1297-1302) (Year: 1954).*
English language translation of Chai ("Study on the Synthesis of Trifloxystrobin"Agrochem. 52(4), p. 258-259, 262, Apr. 2013), dated Dec. 2021 (Year: 2021).*
Chai et al., "Study on the Synthesis of Trifloxystrobin," Agrochem., 52(4):258-259, 262, Apr. 2013.
International Search Report and Written Opinion of the ISA/IN in PCT/IN2018/050560, dated Nov. 22, 2018, 9pgs.

* cited by examiner

*Primary Examiner* — Amy C Bonaparte
(74) *Attorney, Agent, or Firm* — Polsinelli PC

(57) ABSTRACT

The present invention relates to an improved process for the preparation of trifloxystrobin of formula (I), which is simple, economical, efficient, user and environment friendly, moreover commercially viable with higher yield and chemical purity.

(I)

20 Claims, No Drawings

PROCESS FOR THE PREPARATION OF TRIFLOXYSTROBIN

RELATED APPLICATIONS

This application is a National Stage filing under 35 U.S.C. 071 of International Application No. PCT/IN2018/050560 filed Aug. 30, 2018, which claims priority to Indian Patent Application No. 201721032019 filed Sep. 11, 2017, which applications are incorporated herein by reference.

FIELD OF THE INVENTION

The present invention relates to an improved process for the preparation of trifloxystrobin of formula (I) in an environment friendly and commercially viable manner with high yield and high chemical purity.

(I)

BACKGROUND OF THE INVENTION

Trifloxystrobin is a member of strobilurin class of fungicides. Trifloxystrobin is chemically known as [(E)-methoxyimino]-{2-[1-(3-trifluoromethyl-phenyl)-eth-(E)-ylideneaminooxymethyl]-phenyl}-acetic acid methyl ester as represented as formula (I). It is known to possess wide range of fungicidal action with good preventive and curative properties. Taking into an account wide range of activity and commercial interest many synthetic routes leading to trifloxystrobin and intermediates are reported in the literature. They are summarized in the following discussion.

The U.S. Pat. No. 5,238,956 discloses the use of (2-bromomethyl-phenyl)-[(E)-methoxyimino]-acetic acid methyl ester (intermediate 7) as intermediate in target molecule synthesis, without its method of preparation. This patent also discloses conversion of (E,E)-methyl 3-methoxy-2-[2-(methyl(3-trifluoromethylphenyl)oximinomethyl) phenyl]-propenoate to trifloxystrobin in two steps. Origin of the starting material of this reaction is not mentioned.

The U.S. Pat. No. 6,444,850 discloses the novel fungicidal compounds having a fluorovinyloxyphenyl moiety and its process of preparation. The document discloses preparation of (2-bromomethyl-phenyl)-[(E)-methoxyimino]-acetic acid methyl ester (intermediate 7). In this method 2-bromo toluene is converted to intermediate (7) via Grignard reaction, oxime formation, followed by bromination reaction. This intermediate (7) is then converted to trifloxystrobin (Scheme-1).

Scheme-1

Intermediate

Intermediate-6

Intermediate-7

Intermediate

R1 = H, CF$_3$; R2 = H, C1-10 alkyl, naphthyl, thiophenyl, phenyl group optionally carrying one or more substituents Fungicidal compounds with Flurovinyl oxy phenyl moiety

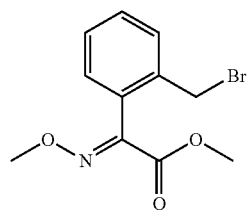

Intermediate-7

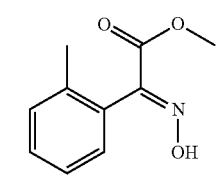

(I)

The drawbacks of the process are as the key raw material 2-bromo toluene is relatively expensive, Grignard reaction needs rigorous dry conditions to be maintained, further (E)-2-methoxyimino-2-(o-tolyl)acetic acid methyl ester (intermediate 6) is converted to bromo derivative (E)-2-(2-bromomethylphenyl)-2-methoxy iminoacetic acid methyl ester (intermediate 7) using reagent N-bromo succinamide (NBS) which is an expensive reagent as compared to other alternatives to bromination reaction.

The U.S. Pat. No. 6,670,496 describes the preparation of [(E)-hydroxyimino]-o-tolyl-acetic acid methyl ester (5A), but further utilization of this intermediate is not clearly mentioned in this patent.

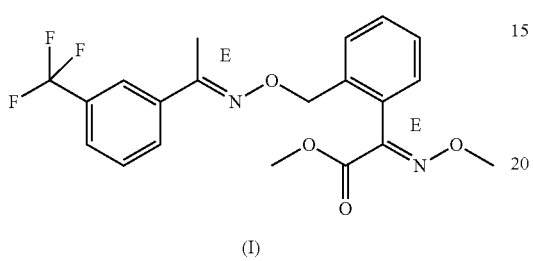

[(E)-hydroxyimino]-o-tolyl-acetic
acid methyl ester (5A)

The PCT Publication No. WO2013/144924 A1 describes the preparation of trifloxystrobin in (Scheme-2) starting from 2-methyl benzoic acid in multiple steps in which this acid is converted to acid chloride intermediate (B) which is then treated with sodium cyanide (NaCN) to produce keto nitrile intermediate. This keto nitrile is then treated with dry hydrochloric acid in methanol to form desired intermediate (C). However, in this step about 25% yield is lost due to the formation of undesired intermediate (D). Moreover, the serious risk is associated with use of NaCN, which may react with hydrochloric acid, or any other acidic residual in the system lead to produce toxic hydrogen cyanide (HCN). The presence of HCN needs to be monitored in step-2 and step-3 to avoid the escape of the same to the surrounding environment.

Scheme-2

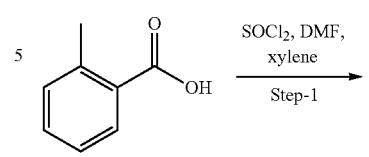

2-Methyl-benzoic acid

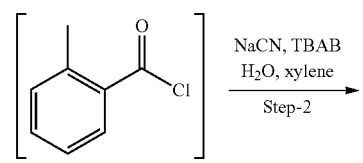

Intermediate-B

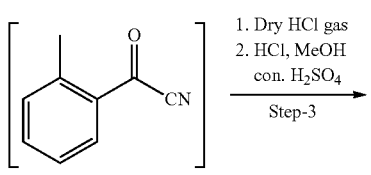

Keto nitrile

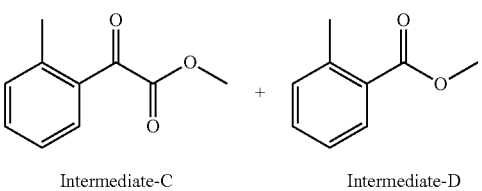

Intermediate-C        Intermediate-D

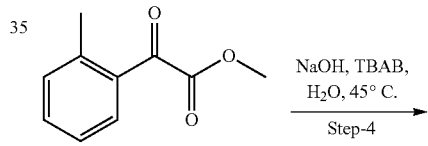

Intermediate-C

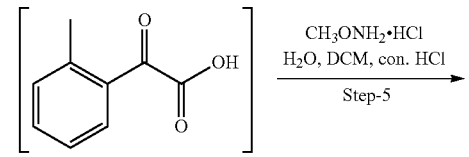

Keto acid

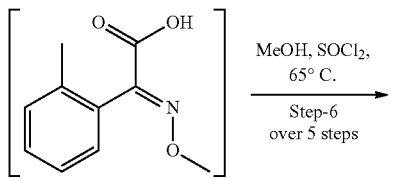

Intermediate-5
(E:Z, ~50:50)

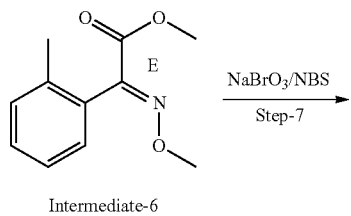

Intermediate-6

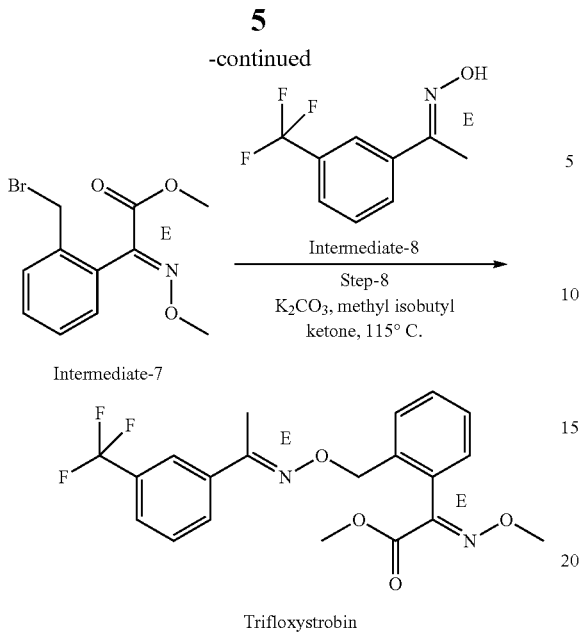

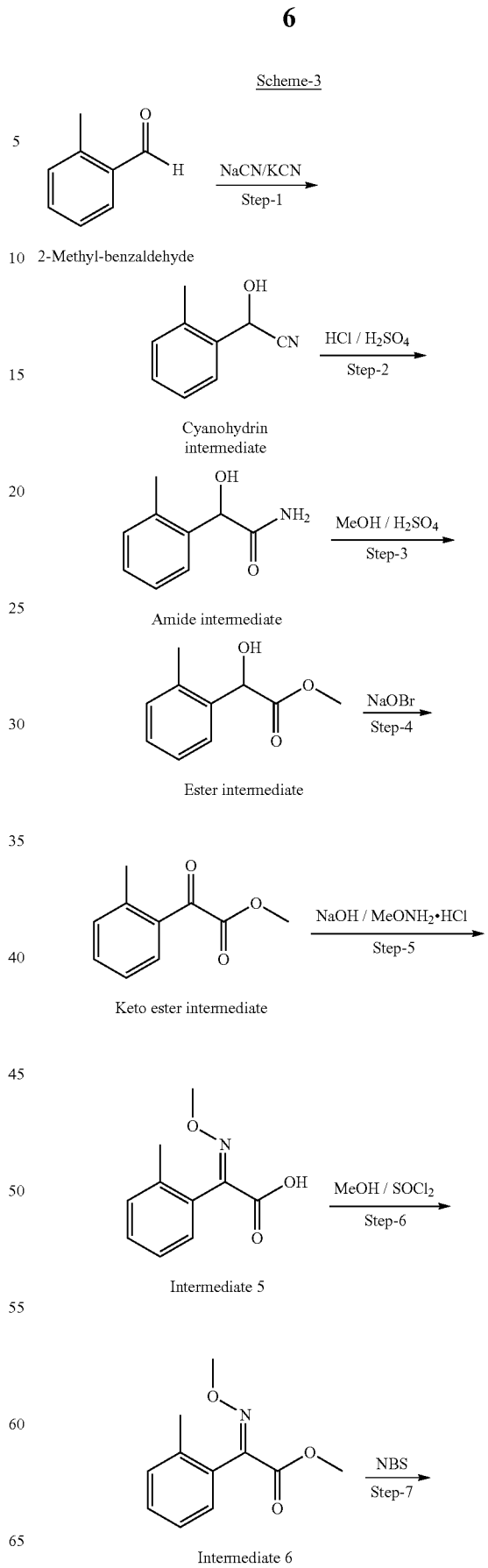

Scheme-3

Further, the formed desired intermediate (C) is present in reaction mixture with intermediate (D), which cannot be separated by physical methods, hence intermediate (C) needs to be essentially and selectively hydrolyzed to give Keto acid which again undergo for the esterification in later stage of the synthesis. Therefore, these additional operations put more burden on this route of synthesis by two extra synthetic steps. The Keto acid thus obtained was treated with methoxyl amine hydrochloride to provide intermediate (5) as E/Z isomeric mixture of about 1:1 ratio. This intermediate (5), then treated with thionyl chloride ($SOCl_2$) and methanol to give ester intermediate (6) in 40% overall yield over (5) steps. Further, bromination of intermediate (6) is resulted to intermediate (7) in 76% yield. Then the intermediate (7) is coupled with intermediate (8) using methyl isobutyl ketone (MIBK) as solvent and potassium carbonate ($K_2CO_3$) as a base at 110° C. to 120° C. to yield trifloxystrobin in 65% isolated yield, which is not satisfactory for commercial operations. Overall yield of this route is only 19% which is not very significant. In this process for preparation of trifloxystrobin, various steps are involved, so overall cycle time for this route is longer and larger amount of effluent is generated by this process, which makes the process more cumbersome.

The PCT Publication No. WO2017/085747A2 discloses a process for the preparation of trifloxystrobin. The 2-methyl benzaldehyde is converted to cyanohydrins intermediate, which is further hydrolyzed to amide intermediate, which is further esterified to give ester intermediate, which further converted in to keto ester intermediate. The same is converted into intermediate (5) and then esterified to give intermediate (6), which was brominated to give intermediate (7). This patent application also describes the coupling reaction of (E)-2-(2-bromomethylphenyl)-2-methoxyimino-acetic acid methyl ester (intermediate 7) with 1-(3-trifluoromethyl-phenyl)-ethanone oxime (intermediate 8) to produce trifloxystrobin (as depicted in Scheme-3). The starting material used 2-methyl benzaldehyde is an expensive raw material.

-continued

*[Intermediate 7: structure of Br-CH2-phenyl with C(=N-O-CH3)-C(=O)-O-CH3 substituent]*

Intermediate 7

+ *[Intermediate 8: 3-(trifluoromethyl)phenyl ethanone E-oxime structure]*

Intermediate 8

→ (Base, Step-8)

*[Trifloxystrobin structure]*

Trifloxystrobin

The afore-mentioned prior art processes for preparing trifloxystrobin, which has certain drawbacks, such as some of the processes contain long synthetic routes, multiple steps along with the use of toxic reagents such as sodium cyanide/potassium cyanide while some of other methods suffered with low yield and economically less viable. Some of the prior art process requires rigorous dry conditions such as those using Grignard reaction. Few prior reported synthetic routes are utilizing more expensive starting materials. Moreover, due to long synthetic routes, there is generation of huge effluent, which consequently increasing the cost of the preparation of trifloxystrobin. Based on the afore-mentioned drawbacks, the prior art processes may be unsuitable for the preparation of trifloxystrobin in commercial scale operations.

To address these shortcomings in the prior art and develop industrially and economically viable process for trifloxystrobin, the present inventors motivated to pursue the instant invention and surprisingly found an improved process for preparation of selectively [(E)-methoxyimino]-o-tolyl-acetic acid (compound 5) in one step and which further converted to trifloxystrobin in a simple manner.

The current invention relates to the selective synthesis of [(E)-methoxyimino]-o-tolyl-acetic acid (compound 5) and further conversion to the same in to trifloxystrobin (I), which is starting from o-toluidine in four simple steps. o-Toluidine (compound 1) is treated with sodium nitrite to produce 2-methyl benzene diazonium chloride (compound 2), which is further treated with glyoxylic acid (E) methoxime (compound 4) in presence of copper sulphate or copper sulphate hydrate to form (E)-2-methoxyimino-2-(o-tolyl)acetic acid (compound 5) in better yields and purity. This compound (5), which is selectively E-isomer is then converted in 3 simple steps to trifloxystrobin in very good yields and high purity (above 98%). The key starting material in this invention is o-toluidine which is inexpensive and can be sourced easily at commercial level. After diazotization of o-toluidine, it is then treated with coupling partner glyoxylic acid (E) methoxime (compound 4, prepared from the compound 3), which is stable and can be isolated as solid product if required. In present invention the compound (5) is made in single isomeric form i.e. (E) the required isomer, which was esterified to (E)-2-methoxyimino-2-(o-tolyl)acetic acid methyl ester (compound 6) using methanol and sulfuric acid or methanol and thionyl chloride in 60% overall yield over 2 steps. The compound (6) was brominated in presence of metal halogenates to produce compound (7). Furthermore, coupling of (E)-2-(2-bromomethylphenyl)-2-methoxy iminoacetic acid methyl ester (compound 7) with compound (8) using acetone as solvent and $K_2CO_3$ base at 20° C. to 30° C. to yield trifloxystrobin in 90% isolated yield. Alternatively, the crude compound (5) can be converted to compound (6) and further to compound (7) without isolation of compound (6) by applying acid-base treatment to the compound (5). This will reduce the reaction time, utility cost on commercial scale. The synthetic steps in current invention are straight-forward and does not require any special equipment. Overall handling and product yield are good and can be reproduced at large commercial scale. The overall yield achieved for the preparation of trifloxystrobin is 40.2% as compared with reported overall yield i.e. 19%.

OBJECTIVES OF THE INVENTION

The main object of the present invention is to provide an improved process for the preparation of a compound of formula (I), which is simple, economical, user-friendly and commercially viable.

Another objective of the present invention is to provide an improved process for the preparation of a compound of formula (I), which would be easy to implement on commercial scale and to avoid excessive use of reagent(s) and organic solvent(s), which makes the present invention eco-friendly as well.

Yet another objective of the present invention is to provide an improved process for the preparation of a compound of formula (I) in a high yield with high chemical purity.

Yet another objective of the present invention is to provide an improved process for preparation of single isomeric form of (E)-2-methoxyimino-2-(o-tolyl)acetic acid (compound 5).

Still another objective of the present invention is that compound of formula (I) can be prepared with or without isolation of compound (5), compound (6) and compound (7).

SUMMARY OF THE INVENTION

Accordingly, the present invention provides an improved process for the preparation of trifloxystrobin formula (I), which comprises the steps of:

(I)

*[Structure of trifloxystrobin formula (I)]* a) obtaining a compound of formula (2) by reacting a compound of formula (1) with alkali metal nitrite in presence of acid;
b) obtaining a compound of formula (4) by reacting a compound of formula (3) with methoxylamine hydrochloride in presence of a base in a suitable solvent or mixture of solvents thereof;

c) obtaining a compound of formula (5) by reacting a compound of formula (2) with a compound of formula (4) in presence of salt of acid or a base and a metal sulphate in a suitable solvent or mixture of solvents thereof;

d) obtaining a compound of formula (6) by reacting a compound of formula (5) with an acid and methanol with or without a suitable solvent or mixture of solvents thereof;

e) obtaining a compound of formula (7) by reacting a compound of formula (6) with metal halogenate in presence of a base with or without catalyst in a suitable solvent or mixture of solvents thereof; and f) obtaining a compound of formula (I) by reacting a compound of formula (7) with a compound of formula (8) in presence of a base with or without phase transfer catalyst in a suitable solvent or mixture of solvents thereof.

The above process is illustrated in the following general synthetic scheme:

requirements. As used in the specification, and in the appended claims, the singular forms "a", "an", "the", include plural referents unless the context clearly indicates otherwise.

In accordance with the objectives, wherein the present invention provides an improved process for the preparation of trifloxystrobin of formula (I) and single isomeric form of (E)-2-methoxyimino-2-(o-tolyl)acetic acid (compound 5).

In an embodiment of the present invention, wherein the said alkali metal nitrite used in step (a) is preferably selected from the group consisting of sodium nitrite ($NaNO_2$), potassium nitrite ($KNO_2$) and the like; most preferably sodium nitrite.

In another embodiment of the present invention, wherein the acid of step (a) is preferably selected from the group consisting of hydrochloric acid (HCl), sulfuric acid ($H_2SO_4$) and the like; most preferably hydrochloric acid.

In another embodiment of present invention, wherein the compound of step (a) having a formula (2) is prepared in in-situ manner.

DETAILED DESCRIPTION OF THE INVENTION

The present invention now will be described more fully hereinafter. The invention may be embodied in many different forms and should not be construed as limited to the embodiments set forth herein; rather, these embodiments are provided so that this disclosure will satisfy applicable legal In another embodiment of the present invention, wherein the said base of step (b) is preferably selected from the group consisting of sodium hydroxide (NaOH), potassium hydroxide (KOH), potassium carbonate ($K_2CO_3$), potassium bicarbonate ($KHCO_3$), sodium carbonate ($Na_2CO_3$), sodium bicarbonate ($NaHCO_3$) and the like; most preferably sodium hydroxide or sodium carbonate.

In another embodiment of the present invention, wherein the said solvent used in step (b) is preferably selected from the group consisting of water, methyl alcohol, ethyl alcohol, isopropyl alcohol, butanol, isobutanol, ethylene glycol and the like or mixture of solvents thereof; most preferably water.

In another embodiment of the present invention, wherein the said salt of acid of step (c) is preferably selected from the group consisting of mono or di sodium, mono or di potassium salt of carboxylic acids such as acetic acid and the like; most preferably mono or di sodium salt of carboxylic acids.

In another embodiment of the present invention, wherein the said base of step (c) is preferably selected from the group consisting of sodium hydroxide, potassium hydroxide, potassium carbonate, potassium bicarbonate, sodium carbonate, sodium bicarbonate and the like; most preferably sodium bicarbonate.

In another embodiment of the present invention, wherein the said metal sulfate of step (c) is copper sulfate and the like.

In another embodiment of the present invention, wherein the said solvent of step (c) is preferably selected from the group consisting of heptane, monochlorobenzene (MCB), isoparaffinic hydrocarbon (Isopar-G) and the like or mixture thereof; most preferably heptane or isoparaffinic hydrocarbon.

In another embodiment of the present invention, wherein the said acid of step (d) is either organic or inorganic acid. The said acid is more preferably selected from sulfuric acid, hydrochloric acid, thionyl chloride and the like; most preferably sulfuric acid or thionyl chloride.

In another embodiment of the present invention, wherein the said solvent of step (d) is preferably selected from the group consisting of monochlorobenzene, ethylene dichloride, dichlorobenzene and the like or mixture of solvents thereof.

In another embodiment of the present invention, wherein the said metal halogenate ($NaXO_3/KXO_3$) of step (e) is preferably selected from the group consisting of sodium bromate ($NaBrO_3$), sodium chlorate ($NaClO_3$), sodium iodate ($NaIO_3$), potassium bromate ($KBrO_3$), potassium chlorate ($KClO_3$), potassium iodate ($KIO_3$), N-bromosuccinimide (NBS) and the like; most preferably sodium bromate.

In another embodiment of the present invention, wherein the said substituent X is selected from the group consisting of chlorine, bromine, iodine.

In another embodiment of the present invention, wherein the said catalyst of step (e) is optionally used, which is preferably selected from the group consisting of sodium bromide (NaBr), potassium bromide (KBr), sodium iodide (NaI), potassium iodide (KI), azobisisobutyronitrile (AIBN) and the like or mixture thereof; most preferably azobisisobutyronitrile.

In another embodiment of the present invention, wherein the said base of step (e) is preferably selected from the group consisting of sodium bisulfite ($NaHSO_3$), potassium bisulfite ($KHSO_3$), sodium hydroxide, potassium hydroxide and the like; most preferably sodium bisulfite.

In another embodiment of the present invention, wherein the said solvent of step (e) in combination with water is preferably selected from the group consisting of ethylene dichloride, dichloromethane, chloroform, monochlorobenzene, acetonitrile, diisopropyl ether, ethyl acetate and the like or mixture of solvents thereof; most preferably ethylene dichloride.

In another embodiment of the present invention, wherein the said base of step (f) is preferably selected from the group consisting of sodium hydroxide, potassium hydroxide, potassium carbonate, sodium carbonate and the like; most preferably potassium carbonate.

In another embodiment of the present invention, wherein the said phase transfer catalyst of step (f) is preferably selected from the group consisting of tetra-n-butylammonium bromide (TBAB), tetrabutylammonium iodide (TBAI), tetrabutylammonium chloride (TBACl), sodium iodide, potassium iodide and the like; most preferably tetra-n-butylammonium bromide.

In another embodiment of the present invention, wherein the said solvent of step (f) is preferably selected from the group consisting of acetone, methyl ethyl ketone, methyl isobutyl ketone, xylene, toluene, monochlorobenzene, propionitrile, acetonitrile and the like or mixture of solvents thereof; most preferably acetone.

In another embodiment of the present invention, wherein the crude compound of formula (I) is purified by crystallization in suitable alcoholic solvent which is preferably selected from the group consisting of water, methyl alcohol, ethyl alcohol, isopropyl alcohol and the like or mixture thereof; most preferably isopropyl alcohol.

In another embodiment of the present invention, wherein any one of the steps or all the said steps from (a) to (f) may be performed in in-situ manner.

In another embodiment of the present invention, wherein all the crude compound is preferably used as such or purified by distillation or crystallization or by different purification techniques well understood by those skilled in the art. The preparation of the starting material used in the present invention are well known in prior art.

The invention is further illustrated by the following examples, which should not be construed to limit the scope of the invention in anyway.

EXAMPLES

Example 1: Preparation of (E)-2-methoxyimino-2-(o-tolyl)acetic acid (Compound 5) in One Step Pot-A The four neck R. B. flask equipped with mechanical stirrer, thermopocket and water condenser was arranged. The water (3.0 vol. w.r.t. o-toluidine) followed by concentrate hydrochloric acid (3.0 vol. w.r.t. o-toluidine) was charged under stirring and cooled the reaction mass to 0° C. to 5° C. o-Toluidine (1.0 eq.) was added drop wise over 30 min to reaction mass under stirring at 0° C. to 5° C. to form off white slurry. This reaction mixture (RM) was stirred for 30 min. The solution of $NaNO_2$ (1.0 eq.) in water (1.0 vol. w.r.t. o-toluidine) was added to reaction mixture lot wise over 30 min at −15° C. to 0° C. After complete addition, the solution was used for the next operation.

Pot-B

To the four necks R. B. flask equipped with mechanical stirrer, thermopocket, water condenser and addition funnel the glyoxylic acid (1.5 eq.), methoxyl amine hydrochloride (1.5 eq.) followed by water (4.0 vol. w.r.t.o-toluidine) was charged under stirring to form clear solution and reaction mixture further stirred at 25° C. to 30° C. for 1.0 h. The solution of the sodium carbonate (2.0 eq.) in water (6.0 vol, w.r.t. o-toluidine) was added lot-wise to reaction mass under stirring. The solution of copper sulphate pentahydrate in water was added to reaction mixture under stirring and further heptane or isoparaffinic hydrocarbon (3.2 vol. w.r.t. o-toluidine) was added. Then RM from Pot-A was slowly added to Pot-B over period of 2.0 h maintaining reaction temperature 15° C. to 30° C. The pH was maintained between 6.5 to 5.0 by addition of aqueous $Na_2CO_3$ solution. The reaction mixture was allowed to stir at 25° C. to 30° C. for 2 h and MDC (10 vol., w.r.t. o-toluidine) was charged and stirred for 15 min. The aqueous and organic layer was separated, extracted the aqueous layer with MDC and combined organic layer was evaporated under vacuum to obtained brown mass (Yield-77% on purity basis, HPLC purity-90%).

$^1$H NMR ($CDCl_3$, TMS) δ (ppm): 7.35-7.09 (m, 4H), 4.06 (s, 3H), 2.18 (s, 3H). $^{13}$C NMR ($CDCl_3$, $CHCl_3$) δ (ppm): 165.4, 149.5, 136.1, 129.9, 129.5, 129.3, 127.9, 129.4, 63.9, 19.4. MS (m/z) $(M-1)^+=192$.

Example 2: Preparation of (E)-2-methoxyimino-2-(o-tolyl)acetic acid (Compound 5) in One Step Pot-A To the four neck R. B. flask equipped with mechanical stirrer, thermopocket and water condenser water (3.0 vol. w.r.t. o-toluidine) concentrated hydrochloric acid (3.0 vol. w.r.t. o-toluidine) was charged under stirring, then solution was cooled to 0° C. o-Toluidine (1.0 eq.) was added drop wise over 30 min. to reaction mass under stirring at 0° C. to form off white slurry and further stirred for 30 min. The solution of $NaNO_2$ (1.0 eq.) in water (1.0 vol. w.r.t. o-toluidine) was added dropwise to reaction mixture over 30 min at −5° C. to 0° C. and after complete addition, the solution was used as such for next operation.

Pot-B

To the four neck R. B. flask equipped with mechanical stirrer, thermopocket, water condenser and addition funnel glyoxylic acid (1.5 eq.), methoxyl amine hydrochloride (1.5 eq.) and water (4.0 vol. w.r.t. o-toluidine) was charged under stirring to form clear solution, the reaction mixture was cooled to 0° C. to 5° C. The NaOH solution (48% solution, 1.3 eq.) was added drop wise to reaction mass under stirring at 5° C. to 10° C. After complete addition of NaOH solution, the reaction mixture was warmed to room temperature and stirred for the 1.0 h. The solid sodium acetate trihydrate (6.0 eq.) was added lot-wise to reaction mixture under stirring and maintained the pH of the between pH 5 to 7. The copper sulphate pentahydrate solution in water (1.0 vol. w.r.t. o-toluidine) was added to reaction mixture under stirring followed by heptane (5 vol. w.r.t. o-toluidine). The reaction mixture from Pot-A was slowly added to Pot-B over period of 2.0 h maintaining reaction temperature at 25° C. to 30° C. and pH between 6.5 to 5.0 by addition of sodium acetate. After complete addition the reaction mixture was allowed to stir at 25° C. to 30° C. for 2 h. The RM was filtered through buchner funnel, the filtrate allowed to settle, and heptane layer was separated. The aqueous layer was extracted with MDC (3×5.0 vol.) and the organic layer is mixed with previously filtered solid and then distilled under reduced pressure to give solid brown mass of Compound 5 (Yield-68% on purity basis, HPLC purity 91%).

Example 3: Preparation of (E)-2-methoxyimino-2-(o-tolyl)acetic acid methyl ester (Compound 6)

To the four neck R.B. Flask with mechanical stirrer, air condenser, thermopocket, water bath the solution of compound 5 (1.0 eq.) in MeOH (3-5 vol. w.r.t. compound 5) was charged. The concentrated $H_2SO_4$ (0.8 eq.) was added slowly drop wise to reaction mixture at 25° C. to 30° C. over 15 min and heated to reflux temperature for 12 h. The reaction mixture was cooled to 50° C. to 55° C. and water (3.0 vol. w.r.t. compound 5) was added lot wise within 1 h. After complete addition of water, the reaction mixture was stirred for 3 h at 20° C. to 25° C. and filtered on buchner funnel, washed the solid with water and dried the crude product. The crude product was dissolved in isopropyl alcohol (1.43 vol. w.r.t. intermediate 5) and the mixture was heated to 60° C. The solution was cooled the to room temperature, stirred for 1 h and further cooled to −5° C. to 0° C. The solid obtained was filtered on buckner funnel and dried to obtained compound 6 (Yield-80% on purity basis, HPLC purity 97%.) The characterization details of compound (6) is as follows:

$^1$H NMR ($CDCl_3$, TMS) δ (ppm): 7.33-7.09 (m, 4H), 4.04 (s, 3H), 3.86 (s, 3H), 2.18 (s, 3H). $^{13}$C NMR ($CDCl_3$, $CHCl_3$) δ (ppm): 163.5, 150.0, 135.9, 130.2, 129.9, 129.3, 127.8, 125.4, 63.7, 52.9, 19.4. MS (m/z) $(M+1)^+=208$. The same reaction was also performed using methanol and thionyl chloride. The isolated yield of compound (6) was 75% on purity basis, HPLC purity 98%. Similarly, compound (5) is first converted to acid chloride intermediate then treated with methanol to yield compound (6) in 86% yield, HPLC purity 94%.

Example 4: Preparation of (E)-2-(2-bromomethylphenyl)-2-methoxy iminoacetic acid methyl ester (compound 7)

To the four neck R.B. Flask with mechanical stirrer, water condenser, thermopocket and oil bath EDC (5.0 vol. w.r.t. compound 6) and compound (6) in 1.0 eq was charged to under stirring at 25° C. to 30° C. to obtain clear solution. The water (3.0 vol. w.r.t. compound 6) was charged into reaction mixture and stirred for 30 min. The $NaBrO_3$ (1.25 eq.) was added slowly to the reaction mixture under stirring to obtain a clear biphasic solution and further cooled to 5° C. to 10° C. The solution of sodium bisulphite (2.0 eq.) in water (2.0 vol. w.r.t. compound 6) was added to reaction mass slowly drop-wise using addition funnel, maintaining reaction temperature at 5° C. to 10° C. for over 1 h. After complete addition, the reaction mixture was allowed to warm to 20° C. to 25° C. and further heated to 70° C. to 75° C. The reaction mass was cooled to 20° C. to 25° C., separated the organic layers and solvent was removed under vacuum to give crude compound (7). The crude-compound was recrystallized using IPA (Yield-77% on purity basis, HPLC purity 97%). The characterization details of compound (7) is as follows:

$^1$H NMR ($CDCl_3$, TMS) δ (ppm): 7.49-7.34 (m, 3H), 7.15-7.13 (m, 1H), 4.32 (s, 2H), 4.06 (s, 3H), 3.87 (s, 3H). $^{13}$C NMR ($CDCl_3$, $CHCl_3$) δ (ppm): 162.6, 148.5, 135.3, 130.0, 129.7, 129.4, 128.3, 128.0, 63.4, 52.6, 30.5. MS (m/z) $(M)^+=286$.

The same reaction was also performed in presence of catalyst azobisisobutyronitrile which completed in one hour (Yield-70% on purity basis, HPLC purity 97%).

Example 5: Preparation of Trifloxystrobin Formula (I)

To the four neck R.B. Flask with mechanical stirrer, water condenser, thermopocket and nitrogen inlet the compound 7 (1.0 eq.), compound 8 (1.05 eq.), acetone (3.0 vol. w.r.t.

compound 7), TBAB (0.05 eq.), K$_2$CO$_3$ (2.5 eq.) were charged under stirring at 25° C. to 30° C. The reaction mixture was stirred at 25° C. to 30° C. for 24 h and filtered through celite bed, washed the celite bed with acetone (3.0 vol. w.r.t. compound 7). The combined organic layer was distilled under vacuum (15 to 20 Torr) at 40° C. to 45° C. to give crude compound. The crude compound was recrystallized using IPA (Yield-88% on purity basis, HPLC purity 99%). The characterization details of compound (I) is as follows:

$^1$H NMR (CDCl$_3$, TMS) δ (ppm): 7.86 (bs, 1H), 7.79-7.77 (m, 1H), 7.59-7.57 (m, 1H), 7.50-7.36 (m, 4H), 7.20-7.18 (m, 1H), 5.14 (s, 2H), 4.02 (s, 3H), 3.81 (s, 3H), 2.21 (s, 3H). $^{13}$C NMR (CDCl$_3$, CHCl$_3$) δ (ppm): 163.0, 153.3, 149.3, 136.9, 135.8, 130.4, 129.7, 129.1, 129.0, 128.6, 128.5, 128.3, 127.5, 125.3, 123.8, 122.5, 74.7, 63.4, 52.4, 12.1. MS (m/z) (M+1)$^+$=409.

The same reaction was also performed at higher temperature (40° C. to 45° C.) and the reaction was completed in 4 to 6 hours. The reaction was also performed in acetonitrile or propionitrile and isolated yield of the compound in formula (I) was increased to 90%, HPLC purity 98.7%.

Abbreviations

AIBN: Azobisisobutyronitrile
CH$_3$COONa: Sodium acetate
CuSO$_4$: Copper (II) sulphate
DIPE: Diisopropyl ether
DMA: Dimethyl acetamide
DMF: Dimethyl formamide
EDC: Ethylene dichloride
Eq.: Equivalent
g: Gram
h: Hours
H$_2$O: Water
H$_2$SO$_4$: Sulfuric acid
HCl: Hydrochloric acid
HCN: Hydrogen cyanide
HPLC: High performance liquid chromatography
IPA: Isopropyl alcohol
Isopar-G Isoparaffinic Hydrocarbon
KBr: Potassium bromide
KBrO$_3$: Potassium bromate
KClO$_3$: Potassium chlorate
KCN: Potassium cyanide
K$_2$CO$_3$: Potassium carbonate
Kg: Kilogram
KHCO$_3$: Potassium bicarbonate
KHSO$_3$: Potassium bisulfite
KI: Potassium iodide
KIO$_3$: Potassium iodate
KNO$_2$: Potassium nitrite
KOH: Potassium hydroxide
K$_2$SO$_3$: Potassium sulfite
L: Litre
MCB: Monochlorobenzene
MDC: Methylene dichloride
MeOH: Methanol
MeONH$_2$.HCl: Methoxylamine hydrochloride
MIBK: Methyl isobutyl ketone
mL: Millilitre
NaBr: Sodium bromide
NaBrO$_3$: Sodium bromate
NaClO$_3$: Sodium chlorate
NaCN: Sodium cyanide
Na$_2$CO$_3$: Sodium carbonate
NaHCO$_3$: Sodium bicarbonate
NaHSO$_3$: Sodium bisulfite
NaI: Sodium iodide
NaIO$_3$: Sodium iodate
NaNO$_2$: Sodium nitrite
NaOBr: Sodium hypobromide
NaOH: Sodium hydroxide
NBS: N-bromo succinamide
PTC: Phase transfer catalyst
R.B. Flask: Round bottom flask
RM: Reaction mixture
rt: Room temperature
SOCl$_2$: Thionyl chloride
TBAB: Tetra n-butyl ammonium bromide
TBACl: Tetrabutylammonium chloride
TBAI: Tetrabutylammonium iodide
Vol: Volume

Advantages of the Present Invention

1. The intermediate (E)-2-methoxyimino-2-(o-tolyl)acetic acid (compound 5) is synthesised in a single step, as compared to prior art process, which has more number of steps.
2. The key raw material of the instant invention such as o-toluidine is common starting material and easily available in large scale at commercial level.
3. In instant invention (E)-2-methoxyimino-2-(o-tolyl)acetic acid is obtained directly in an (E)-isomeric form and it is essential for further conversion into trifloxystrobin, while comparing to other literature processes the present invention is distinct and advantageous.
4. In instant invention trifloxystrobin is produced using lesser number of steps with 40.2% overall yield, while the literature reports many step syntheses with overall yield 19%.
5. The instant invention does not require the use of any hazardous cyanide reagent; therefore, the said process is environment friendly and safe.
6. In literature step (f) was performed at higher temperature about 120° C. using polar high boiling solvents such as DMF, DMA which are difficult to separate from trifloxystrobin. The high temperature reaction causes impurity formations, which results in lower yield (about 65%) of trifloxystrobin. However, the present invention was performed by using low boiling solvents such as acetone at room temperature (20° C. to 30° C.) to produce trifloxystrobin (88% yield).
7. The instant invention produces trifloxystrobin in a high yield (90%) with high chemical purity (98-99.5%).

We claim:

1. An improved process for the preparation of trifloxystrobin of formula (I), comprising the steps of:

a) preparing a 2-methyl benzene diazonium chloride having a formula (2) by reacting 1-amino-2-methyl-benzene having a formula (1) with an alkali metal nitrite in the presence of hydrochloric acid;

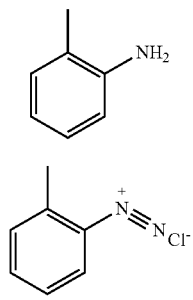

b) obtaining a 2-methoxyimino-acetic acid having a formula (4) by reacting 2-oxoacetic acid having a formula (3) with methoxylamine hydrochloride in the presence of a base in a suitable solvent or mixture of solvents thereof;

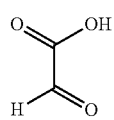

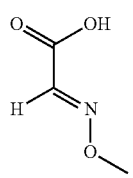

c) selectively obtaining (E)-2-methoxyimino-2-(o-tolyl) acetic acid having a formula (5) by reacting a compound of aforesaid formula (2) with a compound of aforesaid formula (4) in the presence of a salt of an acid; or a base and a metal sulphate in a suitable solvent or mixture of solvents thereof;

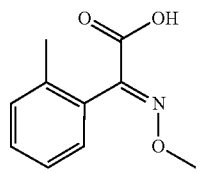

d) obtaining selectively (E)-2-methoxyimino-2-(o-tolyl) acetic acid methyl ester having a formula (6) by reacting a compound of aforesaid formula (5) with methanol and an acid or thionyl chloride with or without a suitable solvent or mixture of solvents thereof;

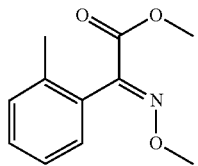

e) selectively obtaining (E)-2-(2-halomethylphenyl)-2-methoxy iminoacetic acid methyl ester having a formula (7) by reacting a compound of aforesaid formula (6) with a metal halogenate or N-bromosuccinimide in presence of a base with or without a catalyst in a suitable solvent or mixture of solvents thereof;

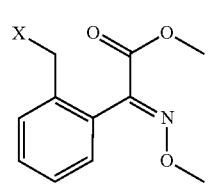

where X = Cl, Br, I f) obtaining the trifloxystrobin of formula (I) by reacting a compound of aforesaid formula (7) with a 1-(3-trifluoromethyl-phenyl)-ethanone oxime having a formula (8) in the presence of a base and with or without a phase transfer catalyst in a suitable solvent or mixture of solvents thereof

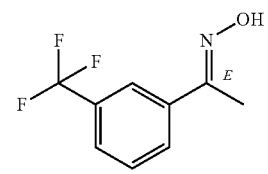

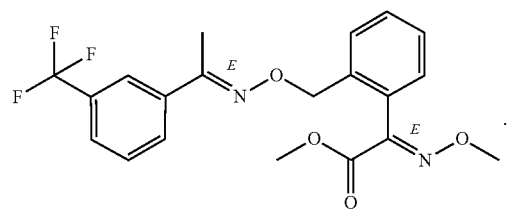

Trifloxystrobin

2. The process as claimed in claim 1, wherein the said formula (2) is prepared in an in-situ manner.

3. The process as claimed in claim 1, wherein the metal nitrite used in step (a) is selected from sodium nitrite and potassium nitrite.

4. The process as claimed in claim 1, wherein the said base of step (b) is selected from the group consisting of sodium hydroxide, potassium hydroxide, sodium carbonate, potassium carbonate, potassium bicarbonate, and sodium bicarbonate.

5. The process as claimed in claim 1, wherein the said solvent used in step (b) is selected from the group consisting of water, methanol, ethanol, isopropyl alcohol, butanol, isobutanol, ethylene glycol, and a mixture thereof.

6. The process as claimed in claim 1, wherein the said salt of an acid of step (c) is selected from the group consisting of mono or di sodium, and mono or di potassium salts of carboxylic acids.

7. The process as claimed in claim 1, wherein the said base of step (c) is selected from the group consisting of sodium hydroxide, potassium hydroxide, potassium carbonate, potassium bicarbonate, sodium carbonate, and sodium bicarbonate.

8. The process as claimed in claim 1, wherein the said metal sulfate of step (c) is copper sulfate.

9. The process as claimed in claim 1, wherein the said solvent of step (c) is selected from the group consisting of heptane, monochlorobenzene, isoparaffinic hydrocarbon, and a mixture thereof.

10. The process as claimed in claim 1, wherein the said acid of step (d) is selected from the group consisting of sulfuric acid, and hydrochloric acid.

11. The process as claimed in claim 1, wherein the said solvent of step (d) is selected from the group consisting of monochlorobenzene, ethylene dichloride, dichlorobenzene, and a mixture thereof.

12. The process as claimed in claim 1, wherein the said metal halogenate of step (e) is selected from the group consisting of sodium bromate, sodium chlorate, sodium iodate, potassium bromate, potassium chlorate, and potassium iodate.

13. The process as claimed in claim 1, wherein the said catalyst of step (e) is selected from the group consisting of sodium bromide, potassium bromide, sodium iodide, potassium iodide, azobisisobutyronitrile, and a mixture thereof.

14. The process as claimed in claim 1, wherein the said base of step (e) is selected from the group consisting of sodium bisulfite, potassium bisulfite, sodium hydroxide, and potassium hydroxide.

15. The process as claimed in claim 1, wherein the said solvent of step (e) is a combination of water and a solvent selected from the group consisting of ethylene dichloride, dichloromethane, chloroform, monochlorobenzene, acetonitrile, diisopropyl ether, ethyl acetate, and a mixture thereof.

16. The process as claimed in claim 1, wherein the said base of step (f) is selected from the group consisting of sodium hydroxide, potassium hydroxide, potassium carbonate, and sodium carbonate.

17. The process as claimed in claim 1, wherein the said phase transfer catalyst of step (f) is selected from the group consisting of tetra-n-butylammonium bromide, tetrabutylammonium iodide, tetrabutylammonium chloride, sodium iodide, and potassium iodide.

18. The process as claimed in claim 1, wherein the said solvent of step (f) is selected from the group consisting of acetone, methyl ethyl ketone, methyl isobutyl ketone, xylene, toluene, monochlorobenzene, propionitrile, acetonitrile, and a mixture thereof.

19. The process as claimed in claim 1, wherein one or all the steps are performed in an in-situ manner.

20. A process for the preparation of trifloxystrobin of formula (I) as claimed in claim 1,

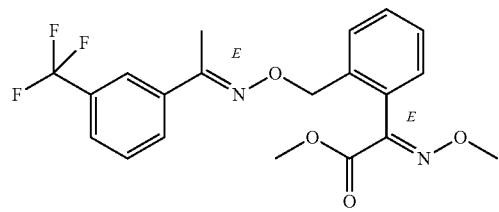

(I)

comprising the steps of:

a) preparing a 2-methyl benzene diazonium chloride formula (2) by reacting 1-amino-2-methylbenzene having a formula (1) with sodium nitrite in the presence of hydrochloric acid;

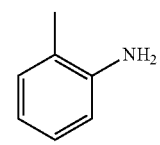

(1)

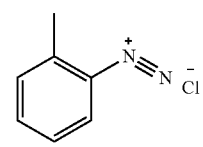

(2)

b) obtaining a 2-methoxyimino-acetic acid having a formula (4) by reacting 2-oxoacetic acid having a formula (3) with methoxylamine hydrochloride in the presence of sodium carbonate in water;

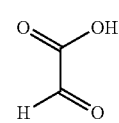

(3)

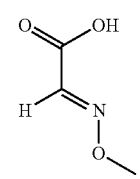

(4)

c) selectively obtaining (E)-2-methoxyimino-2-(o-tolyl) acetic acid having a formula (5) by reacting a compound of aforesaid formula (2) with a compound of aforesaid formula (4) in the presence of a sodium carbonate and a copper sulfate in a mixture of water and heptane;

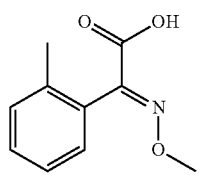 (5)

d) obtaining selectively (E)-2-methoxyimino-2-(o-tolyl) acetic acid methyl ester having a formula (6) by reacting a compound of aforesaid formula (5) with methanol and sulfuric acid;

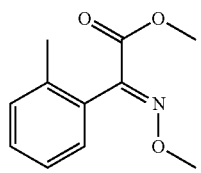 (6)

e) selectively obtaining (E)-2-(2-bromomethylphenyl)-2-methoxy iminoacetic acid methyl ester having a formula (7) by reacting a compound of aforesaid formula (6) with a sodium bromate and sodium bisulfite in water;

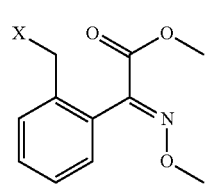 (7)

where X = Br f) obtaining trifloxystrobin of formula (I) by reacting a compound of aforesaid formula (7) with a 1-(3-trifluoromethyl-phenyl)-ethanone oxime having a formula (8) in the presence of potassium carbonate and tetra-n-butylammonium bromide in acetone;

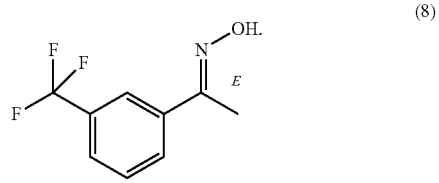 (8)

\* \* \* \* \*